United States Patent [19]

Eberhardt

[11] Patent Number: 5,659,741
[45] Date of Patent: Aug. 19, 1997

[54] COMPUTER SYSTEM AND METHOD FOR STORING MEDICAL HISTORIES USING A CARRYING SIZE CARD

[75] Inventor: Silvio P. Eberhardt, Wallingford, Pa.

[73] Assignee: Stuart S. Bowie, Laramie, Wyo.

[21] Appl. No.: 422,901

[22] Filed: Apr. 17, 1995

Related U.S. Application Data

[63] Continuation-in-part of Ser. No. 413,008, Mar. 29, 1995, abandoned.

[51] Int. Cl.$^6$ .................................................. G06F 17/30
[52] U.S. Cl. ........................ 395/615; 379/93; 379/38; 364/413.02; 364/413.03; 395/610
[58] Field of Search .......................... 235/492, 439; 364/413.02, 413; 283/76, 7; 40/2.2; 379/38, 93; 368/10; 206/37, 232; 395/615; 340/825.54

[56] References Cited

U.S. PATENT DOCUMENTS

| | | | |
|---|---|---|---|
| 3,921,318 | 11/1975 | Calavetta | 40/2.2 |
| 3,958,690 | 5/1976 | Gee, Sr. | 206/232 |
| 4,318,554 | 3/1982 | Anderson et al. | 283/7 |
| 4,621,729 | 11/1986 | Jackson et al. | 206/37 |
| 4,632,428 | 12/1986 | Brown | 283/76 |
| 4,695,954 | 9/1987 | Rose et al. | 364/413 |
| 4,839,806 | 6/1989 | Goldfischer et al. | 364/413.02 |
| 4,868,376 | 9/1989 | Lessin et al. | 235/492 |
| 5,408,443 | 4/1995 | Weinberger | 368/10 |
| 5,451,763 | 9/1995 | Pickett et al. | 235/439 |
| 5,453,602 | 9/1995 | Hanada | 235/492 |
| 5,455,851 | 10/1995 | Chaco et al. | 379/38 |
| 5,465,082 | 11/1995 | Chaco | 340/825.54 |

*Primary Examiner*—Thomas G. Black
*Assistant Examiner*—Charles Rones
*Attorney, Agent, or Firm*—Stuart S. Bowie

[57] ABSTRACT

A computer system and method for programming it for storage of individual medical histories on a storage device, preferably about the size of a credit card, for adding new medical data about the individual to the device and for communicating with other computers to retrieve large data records about the individual; and for enabling a second computer to collate and sort data relating to selected medical fields from the data of such individual and from the data about other individuals transferred to the second computer.

2 Claims, 11 Drawing Sheets

COMPUTER SYSTEM AND METHOD FOR STORING MEDICAL HISTORIES USING A CARRYING SIZE CARD

This is a continuation-in-part of U.S. Ser. No. 08/413,008 filed Mar. 29, 1995, now abandoned.

BACKGROUND OF THE INVENTION

This invention relates to a computer system ("CS") for creating a stored record of the medical history of an individual ("MH"), for adding new medical data ("ND") to the MH of that individual, for organizing MH data, for transmitting data from the system to a remote central data facility ("CDF") and which has many other beneficial functions.

The term "CS" (computer system), is employed herein, unless otherwise indicated, to include a computer, a computer program and a MH memory storage device ("SD"), which may be in the form of a floppy disk or, more preferably, a smaller memory card, preferably the size of credit cards. The memory may be provided magnetically, which is practical with current technology and existing equipment, or may be in many other forms, including optical character recognition systems, laser created and readable systems (such as so-called compact discs) and so on.

The CS makes it possible for an individual's MH to be "read" from the SD by a computer (i.e., the data on the SD is loaded in the memory of the computer, which data is then transferable into the RAM of the computer), to be displayed on the computer's monitor, to be printed via a computer, and makes it possible to transmit the MH or selected portions thereof to other computers, and for searching the MH for desired data.

When the individual is examined by a Physician or other health care specialist such as a Nurse, Paramedic, Emergency Medical Technician, etc.), their observations are added (via so-called "input") to the MH. (Hereinafter, for convenience, Physicians, Nurses and such other health care specialists are collectively called "HCS".)

The need for the present invention and the technical problems solved by it are clear. At present, individuals do not carry on their person any means comprising a complete medical history of themselves. For those who suffer from certain ailments, such as diabetes, there are physical devices, such as wristbands and lockets, to warn HCS of their condition in the event they become unconscious or unable to communicate.

In addition, many individuals are not informed about their own medical history or condition, either because HCS attending them fail to inform them of their medical condition, or because they lack mental or educational capacity to retain or understand information given to them.

Clearly, the CS described will be of enormous benefit to the health care of all persons and the management thereof by HCS.

Further, as will be described, the CS provides means for aggregating vast amounts of data from large numbers of individual MHs (e.g. pharmaceutical information) which now is either not collected or, if it is, only collected randomly or in response to reports of serious incidents.

Using the present invention, such data desirably is transmitted from the SDC of individuals by the HCS and preferably is initially sorted (or otherwise screened) prior to transmission so that the identity of the individual, as well as non-relevant material, is not transmitted.

The transmission is from the HCS' computer in which the MH is stored (on an SD) to a CDF via modem. One practical problem prevalent with the HCS group, especially busy Physicians, is that most prefer to record medical history observations during a patient visit by hand onto paper, often in indecipherable fashion. The problem is thus the means by which such HCS will be induced to input their observations onto the SD for each patient during observation and then promptly transmit desired data to the CDF, if this latter step is in order, and to otherwise perform tasks assigned by the CS as described herein.

This problem is solved, according to one embodiment of this invention, as follows. The CDF management arranges with health insurers and others obligated to pay part or all of individual health charges (these entities are called "insurers" for convenience) to pay the CDF for each MH report received by the CDF. In turn, the CDF, acting in this aspect as a kind of "bank", pays the HCS immediately upon receipt of the MH data. This payment can be by any conventional means, including electronic funds transfer. Of course, since the CDF is forwarding payment prior to receiving payment from the insurer, the CDF will ordinarily discount the payment to the HCS, much as typical bank credit cards do. Such discounts are understood to range from 2–4%.

In that fashion, the HCS has a real incentive to assure that accurate MH data and observations obtained from examining the patient are inputted in the CS, including on the SD, and, further, that data desired by the CDF is immediately transmitted, preferably via modem, to the CDF. The incentive, of course, is immediate payment for the HCS' services to the patient and, possibly, for the data sent.

However, in no known country do all or any significant percentage of citizens carry on their persons any type of device recording their full, complete and up-to-date medical history. Nor is there any computer system to record and manage such information.

As a result, when persons are involved in accidents or collapse in public or private or otherwise become very ill, emergency medical response teams ("EMT") reaching them are compelled to rely on very basic, often non-determinitive, hurried tests to attempt to determine what is wrong with the patient. Notwithstanding the best intentions and efforts, it is often not possible for these EMT personnel to diagnose the patient's problem. Consequently, many patients expire before reaching the hospital.

The same confusion prevails in hospital emergency rooms ("ER"), where attending physicians, residents and nurses often frantically try to decipher an illness or medical condition from obviously very ill patients who are unconscious, unable to speak or, as is the case of many poor and uneducated persons, ignorant of their medical status and history.

In such cases, where the patient's medical history is not readily ascertainable, the HCS are forced to make numerous, time-consuming, often expensive diagnostic tests to determine what is wrong with the patient. This involves substantial expense and loses critical time.

Indeed, in a substantial number of cases, the inability to quickly determine what is wrong with the patient is fatal or causes him or her substantial harm.

At the present time, there is a "health care crisis" in the United States. Moreover, health care costs are imposing severe strains on many other countries. To a large extent, however, this "crisis" is monetary, often called "cost driven". In turn, what has been driving up the costs is the large array of expensive diagnostic tests prescribed by HCS to make their diagnosis. However, these tests are often unnecessary in the sense that many individuals previously have had such tests, or their medical history, if known to the HCS then attending them, would obviate the need for many (sometimes all) of the tests.

SUMMARY OF THE DISCLOSURE

For the foregoing reasons, there is a clear need for a CS of the type described including a SD which can be carried on each person and which can be obtained from the person by the HCS when the individual is being examined or treated. The SD is loaded into the computer (CP) of the HCS, thereby to provide the HCS with a comprehensive MH of that person.

The SD may be a 3.5 inch "floppy" disk which fits into the "floppy" drive of computers such as the ubiquitous PCs found in HCS offices, ER, EMT vehicles and other locations readily available to HCS.

The SD, in another form, may be about the size of a so-called credit card (85 mm×53 mm). In that case, there is provided a peripheral "reader", i.e., a device connected to a data port of the computer and which is designed and built to receive the credit card size SD (hereinafter sometimes called "SDC").

Accordingly, such SDC and SDCs, when carried by citizens and recording their medical history, will avert the dangerous, outmoded situation, wherein MH information is not available in a crisis, as previously described.

Indeed, in view of the expense and fatalities involved, it is not understood why health and medical insurers, health organizations, physicians' groups and the medical care industry generally has not realized that such a CS, together with SDC and SDCs, is desperately needed.

It seems clear that, at a time when medical costs are far outpacing inflation in the USA and other countries, widespread use of such a device will have a dramatic positive effect upon health and cost containment and should avoid the unnecessary loss of life, incorrect treatment, and costly expense.

It is understood that, as a concept, medical cards have been discussed, possibly including during the 1992–94 USA Federal Administration's in camera deliberations concerning health care reform, although it is not believed any specific details about such cards (if any specifics were developed), were ever made public. Similar proposals, expressed only as vague concepts, have been the subject of news articles, but it is unknown what, if anything, came thereof.

What is clear is that, in 1995, a CS of the type herein described is not in use in the USA—or in any other country, for that matter.

in part, this probably stems from technological inability. That is, such cards must use computers. In turn, the computers must be programmed (i.e., they must have "software"). The programs must, for example, be designed to record on SDC:

1. Patient identifier data, i.e., the person's name, residence, telecommunications contacts, family members, relatives, employer, health plan number (if any) and social security number (if any).

2. For the sake of privacy, the record identifier data should be encrypted to preclude unauthorized persons from accessing a given person's medical history.

3. A running medical history, or MH. This history commences with the first Physician or other health care professional the person is examined by. To the extent possible, the results of every subsequent examination by that or any other Physician or HCS is recorded on the SD card.

4. The patient may be prescribed pharmaceutical(s) and/or take over the counter medications or even use illicit drugs. This information is recorded in the "drug" or "prescription" segment of the SD's memory. The program provides means whereby the drug segment of the SD card is transmitted, via computer modem, to a CDF at no charge via a "800" telephone number, or over a computer communication network. The CDF is thereby able to compile vast amounts of data daily about specifics drugs and to report the same to the pharmaceutical companies, as discussed below. A charge can be made for this valuable information transfer, of course, and the program of the CS of this invention provides steps to accomplish compensation.

5. Incentives must exist for the physician or other health care provider to input the results of each exam of every patient on to the SD or SDC (which currently desirably is a magnetic storage medium, easily "read" by modern computers). It is thought that the CDF will, itself, receive sufficient drug data to pay for such inputting of data. In addition, such SD cards will provide safer and less expensive medical care, so health insurers and malpractice insurers are certain to provide for the cost of inputting.

Furthermore, a large number of pharmaceuticals ("drugs") are tested before governmental approval, but are not followed adequately after approval. Indeed, on occasion it is discovered that such drugs have dangerous side effects. This information is reported by physicians and other care givers and eventually gets to the governmental authority and the pharmaceutical company. However, in many cases, this is after many persons are harmed.

A very significant advantage of this invention is that drug reactions, both good and bad (or none) can be aggregated for each drug, as collected via the CS from a very large sample of the population. In this manner, the CDF software will identify very quickly adverse side effects which can then be published in the medical and general media and sent to the pharmaceutical company so that it can transmit warnings to HCS who have prescribed the drug. By use of this CS, therefore, it will be possible to avoid many, possibly most, of the adverse side effects which currently are often not reported or sporadically reported.

Further, unexpected positive side effects of drugs become known to physicians. Eventually, these are reported and the drug is then evaluated for approval for a new use. However, in current practice, this is a slow and almost random process. However, as stated, the CS of this invention provides the pharmaceutical industry with a data collection system which records the effects and condition of each person taking one or more drugs.

Furthermore, patient information is updated every time the patient is examined—and for all patients, not just a selected few.

The pharmaceutical data flow will be augmented each time a patient visits a medical facility (Doctor's office, Hospital, etc) by means of the same being transmitted via modem from the HCS' computer to the computer of the CDF. As indicated, up to the present, it is not believed that any pharmaceutical company has developed and implemented any on-going system for tracking essentially all individuals who take a particular one of its drugs.

Thus, as indicated, there is a great need for a portable SD or SDC or SDI. (Unless otherwise indicated, "SD" shall include "SDCs" and "SDIs").

Accordingly, there is provided a CS which includes a computer, a computer program and a SD onto which MH is placed and from which MH can be read by any computer having the same or compatible operating system.

DETAILED DESCRIPTION OF THE INVENTION

The computer system (CS) of this invention comprises multiple hardware and software components.

As persons with ordinary skill in the computer art will recognize, the flowcharts are ISO 5807 standard Program Flowcharts which employ process symbols, such as boxes and diamonds, to show process or method steps. Lines interconnecting the process symbols show the flow of control.

This type of flowchart is excellent to illustrate how one process leads to the next, or how one process passes control to the next.

The drawings and the accompanying specification clearly teach this invention in an accepted fashion, sufficient to enable a programmer with ordinary skill in the art to develop the source code to actually operate via a selected computer language, which will then be converted into computer machine language which in turn the computer uses to build the software described by the instructions. Alternatively, the source code can be generated by programming software, i.e., by a computer program. One excellent such program is that of the NEXT Corporation.

It is thus unnecessary and unduly limiting to specify a particular computer, or operating system or computer language when using this type of universal technique of teaching the invention. Indeed, this format enables the invention to be converted for many different computers and languages without departing from the scope of this invention.

Figure 1:
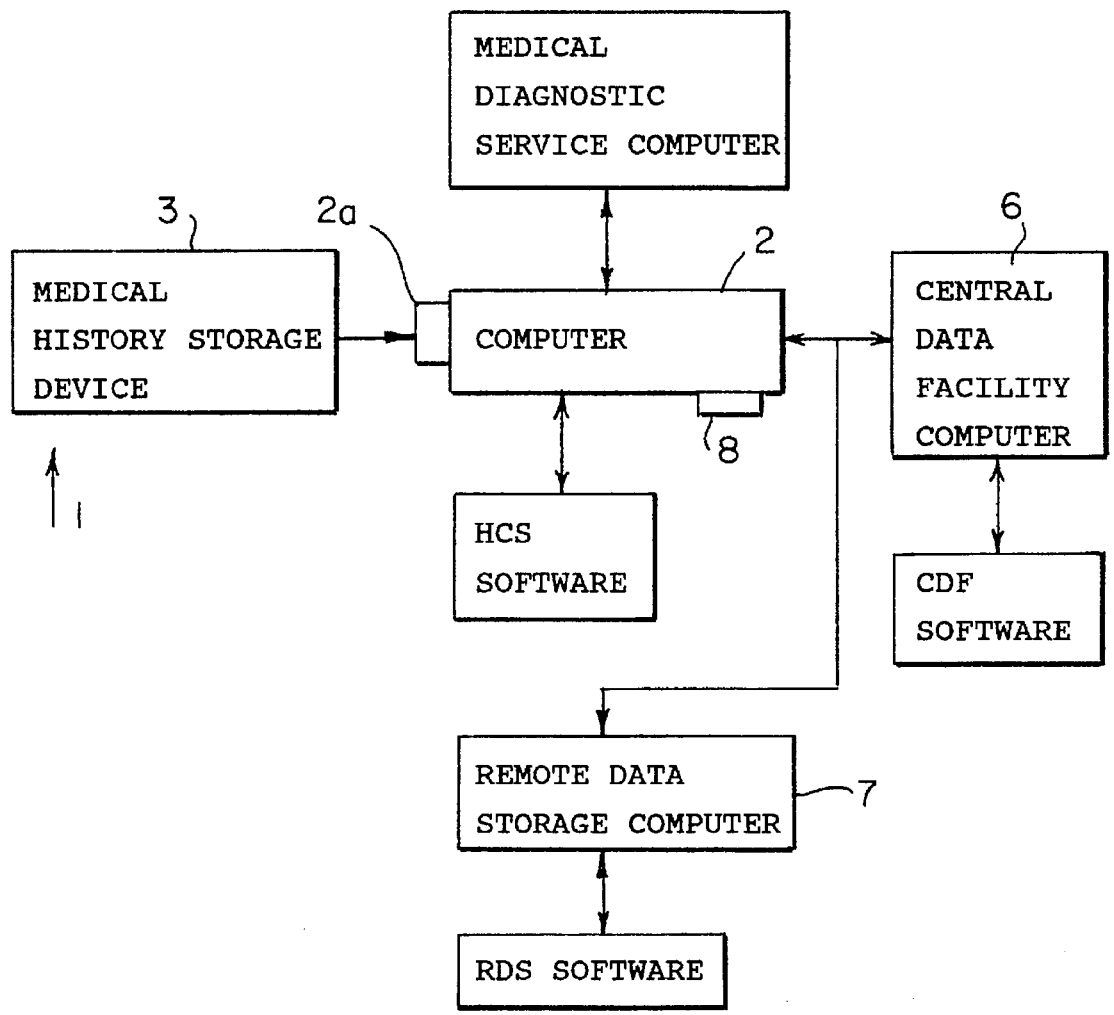
FIG. 1 is a functional flow chart of the system as a whole, showing schematically how the components are connected.
Figure 1A:
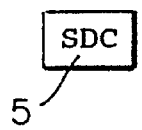
FIG. 1a is a schematic end view of a storage device (SD) of the present invention.

Referring first to one embodiment of the "hardware" which may be employed in this invention, there is shown in FIG. 1 a Medical History Memory storage device, "SD" 1, on which there is stored salient facts of a patient's medical history.

The computer ("CP"), generally shown as 2, which stores MH data on, and receives such data from, the SD 1 may be any of a large number of types. CP 2 may be one of the numerous and widely used personal computers ("PC") or a computer workstation ("WS").

Simply because the majority of PCs are of the so-called IBM-compatible type, the IBM type is a preferred CP 2 for the CS of this invention. However, the CP 2 may otherwise be, for example, a so-called Macintosh (MAC) or many other types of computer. Moreover, computers which can be used with this invention range from very large "mainframe" units, to multi-terminal integrated systems, desktops, laptops, notebooks and hand-held units.

Very preferably, the operating system and graphics subsystem of the CP 2 will support the creation of multiple on-screen windows, menus, and other graphical interface "objects" whose use has become standard in the past few years, especially with so-called point and click devices such as a so-called "mouse". Such objects will be referred to below without elaboration, since they are familiar to anyone skilled in the art of programming or use of a modern human-computer interface.

Indeed, this invention is herein largely expressed in a so-called "windows" environment or mode, primarily because that is the interface which has been so widely adopted in the USA and elsewhere, especially by HCS. Currently, "windows" is the appropriate environment for the "best mode" of describing this invention.

The CP 2 may have a slot 2a for a memory 3. This memory can be standard 3.5 or 5.25 inch so-called "floppy disk" that can be used in this invention as the storage device, SD 1, for an individual's medical history (MH).

This invention also teaches the use of a credit card sized SD, or SDC 5. Because the SDC 5 is much smaller than even 3.5 inch "floppy" disks 3, the slot(s) 2a of the CP 2, which are currently sized to receive the aforementioned floppies, will not receive the SDCs.

Figure 1B:
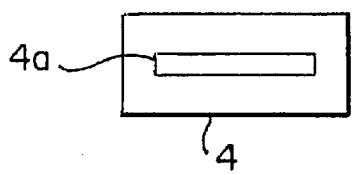
FIG. 1b is a schematic view of a peripheral device for reading data on a SD.

Accordingly, as shown in FIG. 1b, there is provided a peripheral device ("PD") 4, which has a slot 4a which receives the SDC 5. SDC 5 is moved relative to "reading heads" (not shown) within PD 4 which detect information on SDC 5 in magnetized or other readable form, such the optical systems previously described. Information from SDC 5 is converted by PD 4 into computer-readable signals which flow into CP 2.

In lieu of PD 4 and SDC 5 as described above, there may be employed a PCMCIA interface, such as that sold by JDR Microdevices of 1850 South 10th Street, San Jose, Calif. 95112-4108 ("JDR"). In this case, the SD comprises a PCMCIA memory card 3 which is a solid state module, about the size of a credit card and which can store information and which can be written onto. A PCMCIA static RAM card with a battery will function well for the purposes of this invention, as will so-called "flash" PCMICA cards, although the latter are more expensive than the former. Such cards, as sold by JDR and, in their current versions, have memories of 512 Kb to 20 Mb, are suitable for this invention.

Alternatively, the SD may incorporate other types of semiconductor memory (not shown) which can be written to and read by a computer of the type used in this invention.

There is also provided a large computer, called a Central Data Facility (CDF) 6 which can be connected to the CP 2 via modem (shown schematically as 8 in the drawings) or network connection (not shown).

As used herein, a "modem" or a "connection" device refers broadly to the large range of electronic devices which, together with suitable communications software, comprise means whereby a computer can exchange information with another computer via so-called "hard" telecommunications lines, or via radio frequency or other electromagnetic or optical systems.

While a rather large text document may be stored on a 3.5" floppy disk, many modern medical procedures often generate prodigious amounts of data. A single Computer-Aided Tomography (CAT) scan sequence, for example, would fill many floppy disks. It is impractical to store images, video, and sound recordings on the SD 1. Thus, this invention provides means for storing data-intensive files on large memory systems which memories may be on-line or off-line with retrieval on request (e.g. on backup magnetic tape).

Such a large memory means is herein called a "Remote Data Storage Facility" (RDSF) and comprises a computer (CP) 7. CP 7 is programmed to accept data records with arbitrary formats, and can associate each record with a unique identifier string stored on the SD 1.

Standard mechanisms allowing arbitrary data files to be transferred to and from the RDSF 7 are widely available (e.g. using the standard Internet File Transfer Protocol (FTP) mechanism). Thus, no new technology is necessary to implement RDSCs. Indeed, when it is desirable or necessary, the HCS uses the CP 2, loaded with a patient's SD 1, to retrieve such large data records via modem, from the RSDF 7. These records may also be retrieved by use of the CDF 6.

As noted, the preferred embodiment of the Medical History Memory or SD 1 today is a 3.5" diskette, although it is anticipated that advances in memory technology will decrease the cost of other memory systems which may be advantageously employed with this invention. This will allow the use of, for example, inexpensive credit-card sized SDCs 5, and solid-state, optical, or other types of memory devices in the present invention.

Figure 1C:
FIG. 1c is a partial schematic view of a portion of a human upper torso and arm with a Sd implanted under the skin.

It is further within the scope of this invention to implant a small solid-state SDI 11 under a patient's skin, as shown in FIG. 1c, wherein an electromagnetic pickup (not shown) will be used to for through-the-skin communication between the SDI 11 and the CP 2. As a variant, such a small SDI (not shown) could be carried in the chamber of a bracelet or locket.

SD 1 preferably comprises multiple independent files. The most important is the Medical history File (MHF) of the patient, which preferably is divided into records sorted by date. It is advantageous to make the MHF write only, so that records can only be added, not edited or deleted.

A second file stored on the SD 1, defined herein as the "Critical Information File" (CIF), contains critical medical information about the individual. The CIF is maintained as a separate file from the MHF. The CIF functions to allow a HCS, especially in an emergency medical situation, to quickly ascertain important facts about the patient, such as blood type, medical conditions, allergies, sensitivities to drugs and environmental factors, and current prescriptions.

It is contemplated that the CIF will be written (or dictated) by a HCS and will contain instructions for caring for the individual in an emergency. For example, if an individual has restricted arteries, the CIF would indicate this and the desirable emergency treatment, such as the quick administration of nitroglycerine.

The format of a record may be predefined or arbitrary. There are a number of advantages to requiring the health professional to fill in specific items, while at the same time allowing an arbitrary-length "comments" field. One advantage of predefined fields is that searches can be constrained to particular fields, thus limiting the scope of searches. Another is that the HCS would be forced to fill in the most relevant information. Such fields may include Symptoms, Tests Administered, Test Results, Diagnosis, and Prescriptions.

One unique aspect of the present invention is the Central Data Facility (CDF) 6, which can function to collect the medical records of patients associated with member physicians via modem transmissions from such physicians or other HCSs in the manner described.

The CP 2 at the location of the HCS is, if desired, connected to the CDF 6. As will be described below, the connection may be automatic (e.g., via network) when desired, such as when a new record data, ND 18, is added onto a SD 1. In fact, new record data, ND 18, can be added to the CDF 6 even in the absence of a SD 1 connected to the CP 2. This is desirable because diagnostic test results often become available only after a patient has left the test facility. Also, it allows extending a patient's history even if the patient forgets to bring the SD 1 to the HCSs office. In such an event, the SD 1 is automatically updated the next time that it is used in the CP 2 of this or other CS, by way of a data synchronization operation.

In addition to collecting and on occasion dispensing medical histories, the CDF 6 has the capability to search multiple histories for requested events in a general manner, so as to allow epidemiological studies to be carried out on the data.

For example, a search may request that the records of all subjects that were prescribed a certain medication be examined, and that all medical conditions occurring within a selected time period of the prescription be collated.

It is considered that this function of the CS of this invention will provide means whereby, for the first time in history, the reactions (good, bad or none) of a very large group of patients taking a given medicine can be monitored continuously by computer and then the results can be rapidly reported to the pharmaceutical or other manufacturer of the medication. This is in contrast to the present system wherein drug companies do not have any systematic means for collecting on-going information from persons using their drugs.

As previously mentioned, to ensure privacy, a patient's name is not be used in CDF 6 records. Instead, the HCS, when a patient first is given a SD 1, assigns that patient a unique identification code (ID). The ID code is stored in the SD 1. Thus, only the health professional (and, when the patient consents, the patient's health insurance provider) have the lists that correlate patient ID codes with the subject's name.

Below are described in detail the major software components of the present invention: the program that executes on the HCSs CP 2, and the program that executes on the CDF 6 computer.

Figure 2:
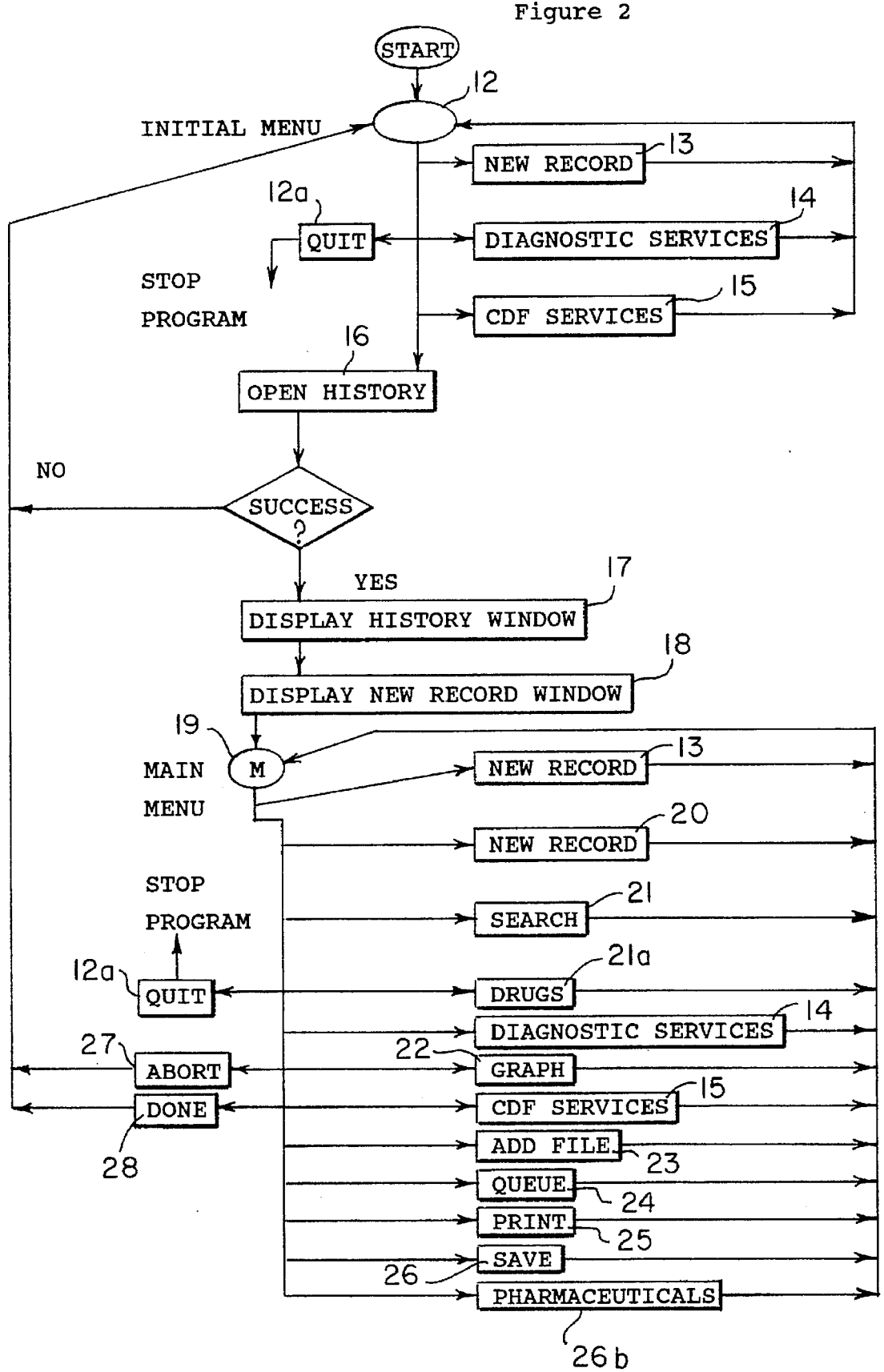
FIG. 2 is a flow chart of the initial and main menu program paths.

Considering first the basic operation of the CP 2 program, as shown in FIG. 2, when this program is newly initialized, no medical history has been transferred into the RAM memory of CP 2. At that stage, the only actions available to the HCS a user are via menu 12 options.

Initial menu operations include the following and the steps involved are depicted schematically by boxes or other accepted programming geometric shapes which are numbered in the drawings. Thus, one step is opening a Medical History File (MHF) 16, another step is specifying or creating new medical data (ND) for the patient, then adding a the ND record to the medical history file 13, communicating ("interacting") with a medical diagnostic service 14, and accessing services on the CDF 6, as at 15, such as examining financial records or performing database searches. These steps for using the CS of this invention are described in more detail below. Also, a "Quit" step 12a causes the program to stop executing and removes all menus and windows associated with this program.

To allow a HCS to access a patient's MH, the HCS must first solicit, or open, a specified history, or, in the case of a new patient, to create a new history for such new patient. This is achieved via step 16. In turn, that step activates other steps of the program. Once a MH has been successfully opened, two windows are created.

The MH History window 17 displays a one-line summary of each record in the MH, preferably with the most recent record displayed first. The New Record window 18 is a multi-field form designed for the steps of compiling the data and information constituting a New Record. Each of these steps is described below in greater detail.

With a MH open, additional menu items 21–28, appear. These options are part of the Main menu 19 and are options that remain available during subsequent manipulations, until Quit, 12a, Abort 27 or Done 28 are selected by the HCS.

The new menu items (which represent method steps) include New Record 20, Search 21, Graph 22, Add File 23, Queue 24, Print 15, Save 26, Abort 27 and Done 28. All but Abort are described below. Abort simply allows quitting the MH without modification (beyond CDF data synchronization), reverting program control to the initial menu 12.

Figure 3:
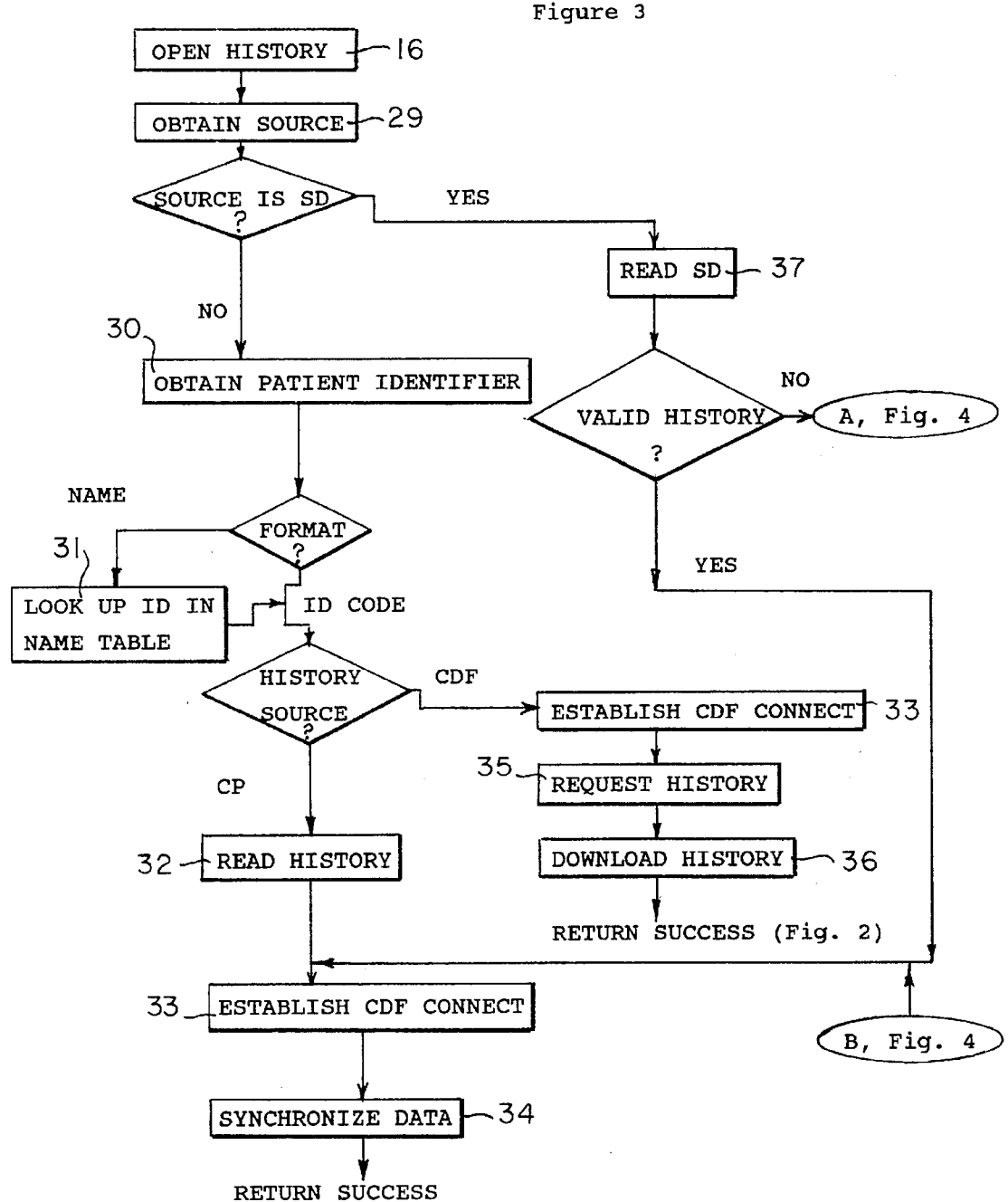
FIG. 3 is a flow chart of the operations relating to obtaining and opening a medical history.
Figure 4:
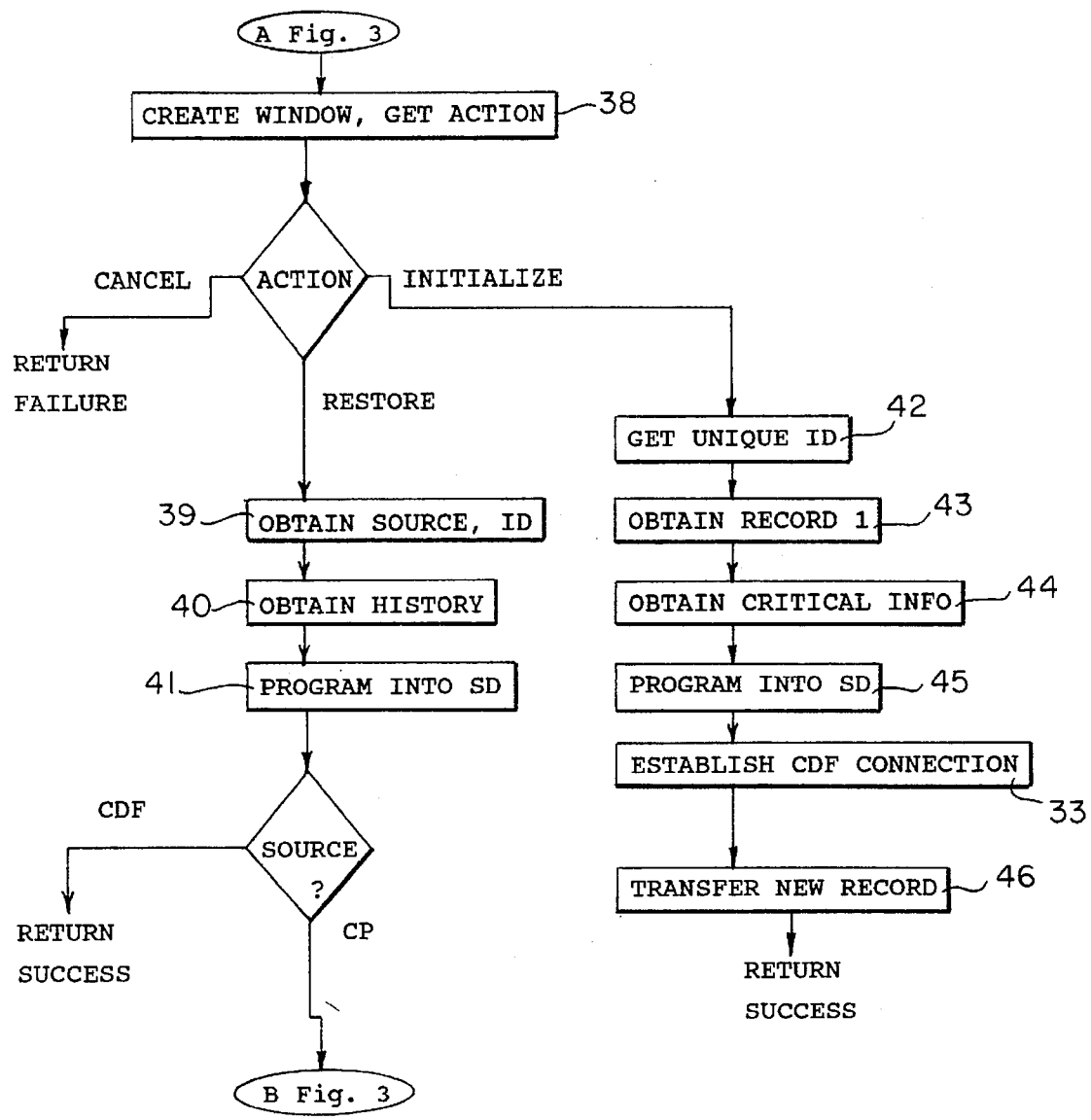
FIG. 4 is a flow chart of the operations for initializing a medical memory on a storage device.
Figure 5:
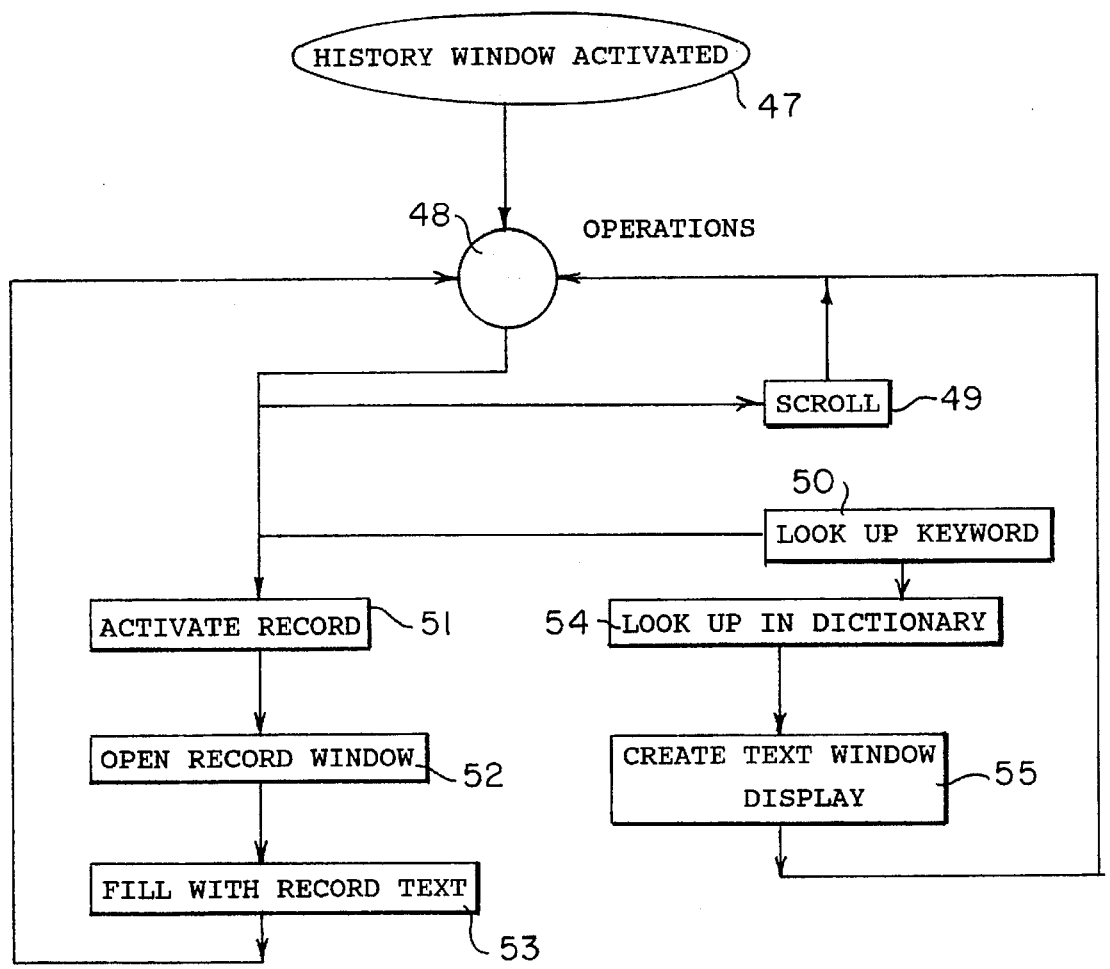
FIG. 5 is a flow chart of operations of the History window that displays summaries of records in the medical history.

The individual components of this high-level description will now be described, starting with the sequence of steps of opening a MH 16, as shown in FIGS. 3 and 4. To open a MH as at 16, the program first performs step 29 to obtain the source (i.e., location) of the medical history, which can be from either the SD 1, the CDF 6, or a directory on the CP 2 hard disk or mass data backup systems.

In accessing the latter two sources, a patient identifier obtained from the HCS by the CS, is employed. The identifier can be the MH ID or the patient's name. If the name is given, a file relating patient names to ID numbers is searched via step 31 to determine the patient's corresponding ID number.

If the source of the MH is the CDF 6, a modem connection 33 is established with the CDF 6, and the MH identified by the ID number is requested 35 from the CDF. The history is downloaded in step 36 across the data connection from the CDF 6 into the CP 2 RAM memory.

If the history source is the CP 2 memory (requiring that the HCS had previously elected to retain the history), the MH is transferred in step 32 into the CP 2 memory.

A data synchronization step 34 is then performed if the MH source is the SD or CP 2 memory. Data synchronization is necessary because some copies of a MH may be modified (i.e., updated) without all other copies being up dated. Synchronization step 34 is achieved by requesting the history in question from the CDF 6 and then comparing records of the two copies of a MH. All records present in one history but not the other are copied so as to bring both copies up-to-date.

It is to be noted that synchronization introduces the possibility that records may occasionally be written in the wrong order.

The other source of the MH is the SD 1. To transfer a MH, the SD 1 is connected to the CP 2 and the stored information is transferred via step 37 to the CP 2 RAM memory.

If the SD 1 was programmed with a valid history, data synchronization step 34 is performed to complete the Open operation. If, however, the SD 1 has not been programmed, or has been rendered unreadable, the sequence of events illustrated in FIG. 4 occurs.

Thus, as the first step, a window 38 pops up notifying the user that the SD 1 memory is not valid. Buttons (images on the windows screen on which the user can "click" a Mouse to cause a desired programmatic action) within this window allow the user to select whether the history is to be restored from memory, whether a new history is to be initialized, or whether to cancel the interaction with the SD 1.

If the selection is to restore the memory's contents, the source of the history backup and the patient's ID code must be obtained via step 39, then the specified history is transferred into the CP 2 RAM memory 40, and finally that history is written in step 41 to the SD 1.

If the history originates from the CP 2, data synchronization 34 is performed with the copy of the MH resident in CDF 6 before writing the MH to the SD 1.

When the SD 1 is initialized with a new MH, several data records must be entered. First, as mentioned, a unique ID code identifier is obtained in step 42 from the HCS. It may be more convenient or reliable to have the CDF 6 automatically dispense all new ID codes, although this particular step is not shown.

Next, the first record of the MH is obtained 43. In many cases, the HCS will input into the record a patient's known previous medical history. Also, the first record will receive input of basic facts about the patient, such as date of birth, race, gender, etc. Such data may thereafter be used during CDF 6 database searches.

Finally, data for the critical information file (CIF) 44 is input into the CP 2.

The first history record 43 and the CIF data 44 can be loaded into CP 2 directly using a standard text editor (not shown) or can come from a previously-created text file (not shown). Files 43 and 44 are then written, as at 45, to the SD 1, and also transferred in step 46 to the CDF 6 after a modem connection 33 is established. This completes the Open History 16 menu operation.

Once a medical history has been loaded into the CP 2 memory, the History window 17 and the New Record window 18 are created. The History window 17 displays a one-line text summary for each record in the history, starting with the most recent record.

The preferred summary format indicates, for a given patient, the date of the record, a short code indicating the type of event (office visit, hospital stay, laboratory test, etc.), symptom(s), diagnosis rendered, pharmaceuticals prescribed and other directions given to the patient. Each line may be color-coded to indicate the urgency of the event. If the text in a particular field, such as symptom, exceeds the number of spaces allocated in the summary line, the field text may be truncated, or an intelligent search can be used to find the most significant keywords (e.g. ache, coronary, neural) in the field. These keywords are then listed alone.

Several operations 48 are available (in addition to the main menu commands) once the user activates, via step 47, the history window 18. In the PC and Macintosh computer systems, this is accomplished by bringing the cursor into window 18 (and possibly clicking the mouse button at that location). A scroll bar 49 allows the HCS to peruse successively earlier records not initially visible in the window.

Other standard operations such as closing, miniaturizing, moving and re-sizing the window are not shown, but are available for all windows within this invention. One of the important actions is clicking on the date of a summary to obtain the full information of the record, as in step 51. A Record Window 52 is opened (or reused, at the preference of the user) which displays the complete text contained within the record, including the comment field.

Figure 6:
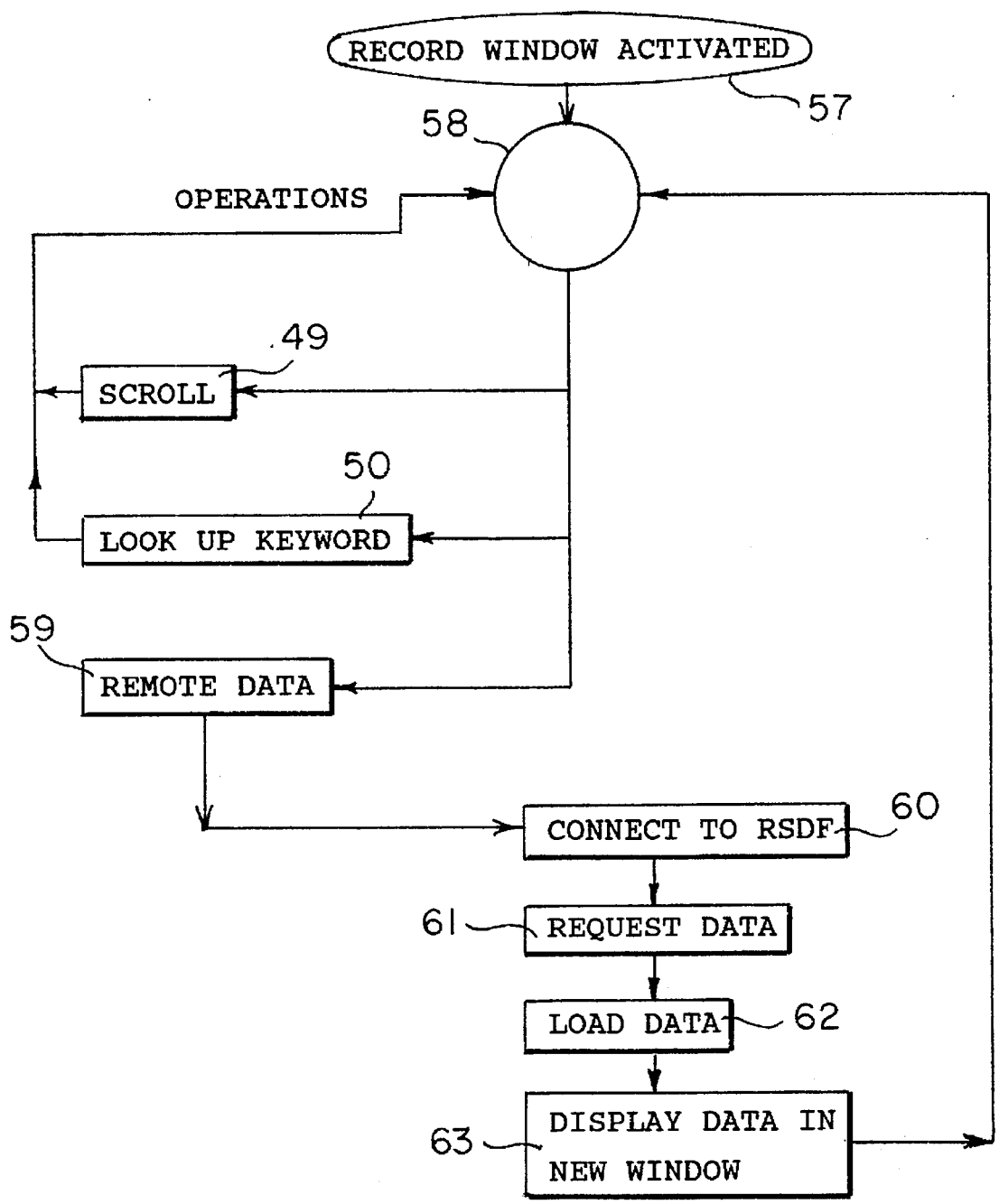
FIG. 6 is a flow chart of operations of the Record window that displays the information in one medical record.

FIG. 6 shows the operations available when a Record Window 52 is activated. A scroll bar 49 is used for perusing larger records. If a portion of the record is stored elsewhere, on a RDSF computer, a signal or flag indicates that. The flag may be, for example, a colored identifier.

If the user clicks on the identifier 59, the system will attempt to connect 60 Record Window 52 to the RDSF 7 computer via modem and read, as at 62, the requested data 61. The data format must then be determined, such that a compatible "window" type may be created for display of the data. Data types may be text, images, video, sounds or other sampled signals.

A system can also be set up for billing (debiting) the HCS for use of the data obtained from the RDSF and/or the CDF 6. In this case, the ID and password of the HCS is sent as part of the request for data. If there are costs associated with the data transfer, a new window is used to alert the HCS to the amount, and the HCS can then continue or abort the operation.

The last action is available in both the History Window 16 and the Record Window 17 as keyword lookup 50.

Clicking (via mouse) on a medically-related keyword (including a pharmaceutical name) causes a dictionary lookup 54 of the keyword, which a text window 55 then displays. For a pharmaceutical drug, the reference material can be stored in the CP 2 itself, or can be loaded over a communication channel from the CDF 6.

If the user activates the New Record Window key, moves the cursor to a field within the record and clicks the mouse button, text can be entered into that field, primarily about the patient. Text of arbitrary length can be entered into the comments field, but other fields may be limited to only one line. If the patient has several independent symptoms or tests, multiple copies of the New Record window can be created with the New Record (NR) 20 menu operation. The NR window also supports use of the dictionary lookup facilities, as at 50, 54 and 55.

The main menu Search operation 21 is important because it allows a HCS to search a MH for particular elements 'such as symptoms, diseases, prescriptions, diagnostic tests, etc. This allows the HCS to scan the development of a particular illness over a specified time interval, for example, or to evaluate a patient's long-term health.

Figure 7:
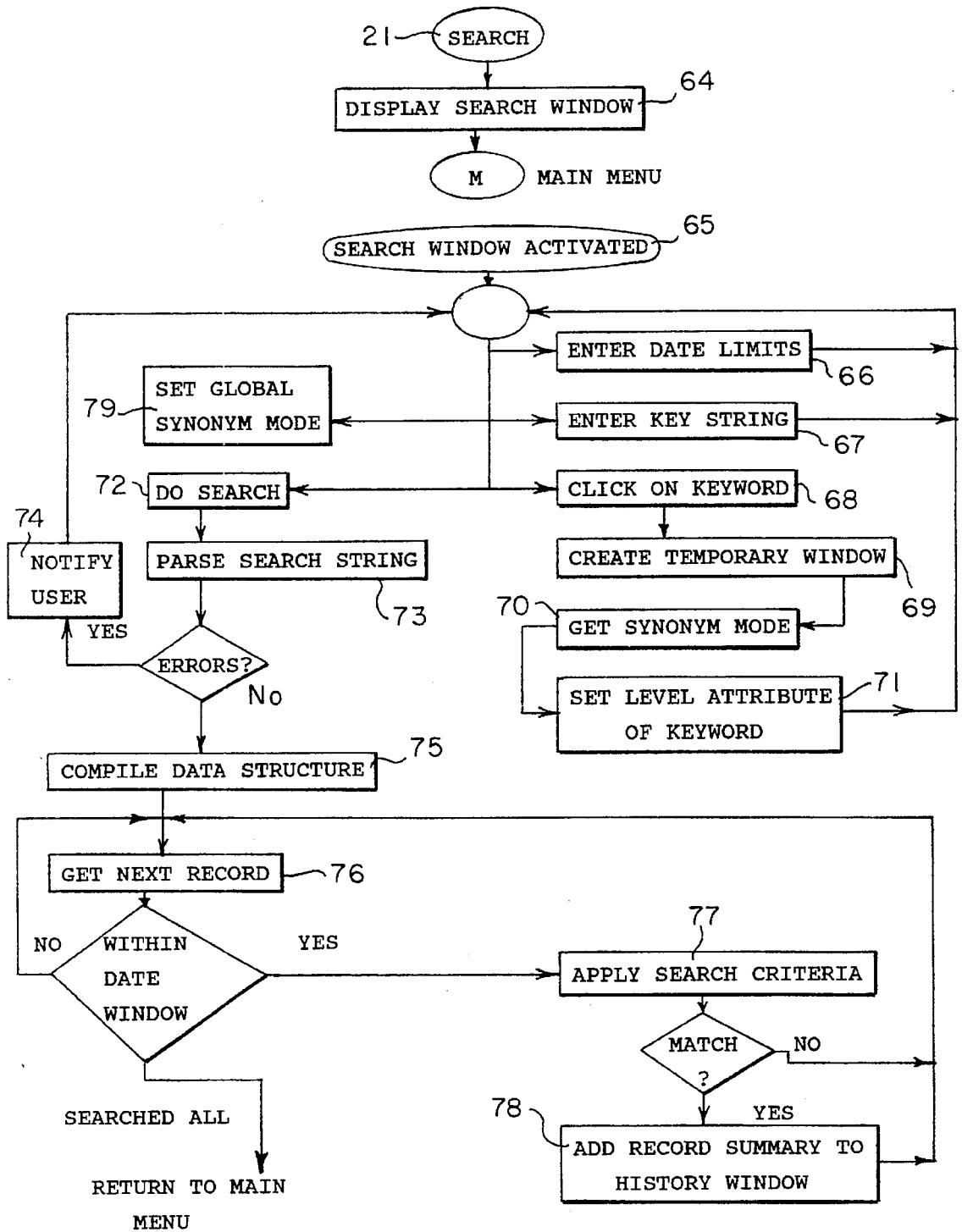
FIG. 7 is a flow chart of Search facility operations.

As shown in FIG. 7, the search operation 21 involves displaying a Search window 64 that allows the user to enter a text string that specifies the desired information to be searched for. The search window contains at least two fields, the DATE field and the KEY field, and a "Conduct Search" button. Once the Search window is activated 65, entering a minimum and a maximum value into the Date field 66 allows limiting the search to a range of dates; only the history records within this range are searched. Dates entered may be absolute (e.g. "Mar. 5, 1980" to "Mar. 5, 1995"), relative (e.g. "present-10 yrs" to "present"), or may be given as an age range of the patient (e.g. 30 y–40 y, where year, month, week, day and hour can be given as y, m, w, d, h, respectively).

Entering a character string (hereinafter sometimes referred to as a "key" string) into the Key field 67 allows a user to specify one or more keywords to be searched, separated by Boolean operators such as AND, OR and NOT. Parenthesis may be used to group clauses. Additionally, each keyword may optionally be prefixed with one of the field names of the record structure, followed by a colon. This limits the search for that keyword to within the specified field; if a field is not specified, the keyword is matched with all words in the record. For example, the key string syntax: (back AND (pain OR ache)) AND diagnosis: strain would retrieve records in which the patient complained of back pain and was diagnosed with back strain.

Each record is independently searched to determine whether the key string matches the record. By the principles of Boolean Logic, a keyword is evaluated as TRUE if the word is found in the specified field of a record, or in the record as a whole if a field is not specified. Clauses formed with the AND operator are true only if the preceding and following keywords or clauses evaluate to true, and clauses formed with the OR operator are true if at least one of the preceding and following keywords or clauses are true. A NOT operator applied to a keyword or clause reverses the true/false evaluation.

When the user clicks on the "Do Search" button 72, the key field is parsed 73, error checked, and organized into an internal data structure that allows efficient execution 75. If there are syntax errors, these are displayed to the user in a new window 74. Otherwise, this data structure is applied to each record 76 in the date range to determine whether the record matches the requirements of the key string 77. The summary lines for all matched records are placed into 78 the History window 17, which is first emptied.

Alternatively, the user can set a default parameter that causes all records to be retained in the History Window, with the matched record summaries colored differently from the unmatched, or otherwise identified.

An extension of the search operation allows a user to specify independently for each keyword that one or more synonyms be searched in addition to the keyword. This allows more precise searches because ambiguities in the wording of records may be largely overcome. For example, pain may be substituted for ache, or a prescription may be substituted with a chemically equivalent compound from another vendor.

The preferred implementation allows several levels of synonym usage (or modes), such as: "no synonyms", "closely related", "related", and "loosely related". "Closely related" might allow substituting the medical term for the common terminology, while "loosely related" might in addition allow substituting nearby body parts (i.e. "hand" for "arm"). A dictionary for such relationships can be compiled for any of types of information that would be entered into a record.

The user can specify in three ways that synonyms be used: 1) A global preference parameter programmed by the user as step 79 which sets one of the synonym modes as the default for all keywords; 2) The Search window contains another field that contains "radio" buttons that allow specifying exactly one of the synonym modes for the scope of that particular search 79; and 3) Double-clicking on a keyword 68 brings up a window that allows obtaining from the HCS 70 and setting 71 the synonym mode for only that keyword. Keywords can be colored to indicate their synonym mode.

Operation of the synonym option is straight forward: Any keyword with an associated synonym mode is applied to an electronic synonym dictionary residing on the CP 2. This dictionary is used to obtain the synonyms of each keyword at the desired mode. Each keyword in the data structure 75 is then replaced by a clause that consists of the keyword OR-connected with all its synonyms. Field identifiers, if given for a key word, are inherited by the key word's synonyms.

The Search window can be further extended to allow graphing some functions occurring across records. For example, blood pressure can be plotted over a period of 10 years. This graph mechanism can be included as a main menu item 22 separate from Search 21, or can be permanently combined with the Search operation.

The Graph operation requires that a new field be added to the window configuration described as the search window 64. This field is called quantity, and gives one or more keywords that describe the item to be graphed. A Boolean AND operation exists between the keywords of he quantity field. Each keyword can be associated with a synonym mode, in a manner identical to the synonym features of the search operation. This feature allows different descriptions of the same diagnostic tests to be detected (e.g. blood pressure, bp, systolic, diastolic).

The items to graph may or may not have numerical values associated with them. In either case, the graph's dependent axis is the date of the record that matched both the key string (if given) and the quantity. If no numerical value follows the keyword, a distinctive mark is drawn at the appropriate date at the midpoint of the independent axis. This allows the user to identify patterns in time (e.g. a symptom of leg pain or usage of a particular drug).

If one or more numbers follow the keyword or its synonyms, these numbers are placed in memory, along with the record date. After all the records in the specified time frame are searched, the minimum and maximum values in the lists are identified, and these values are used to create the dependent axis indices. The values stored in the list are then plotted. The plot is drawn in a newly-created window. Multiple graph windows may exist simultaneously, since each time the Graph operation is selected, a new Graph window is created.

Figure 8:
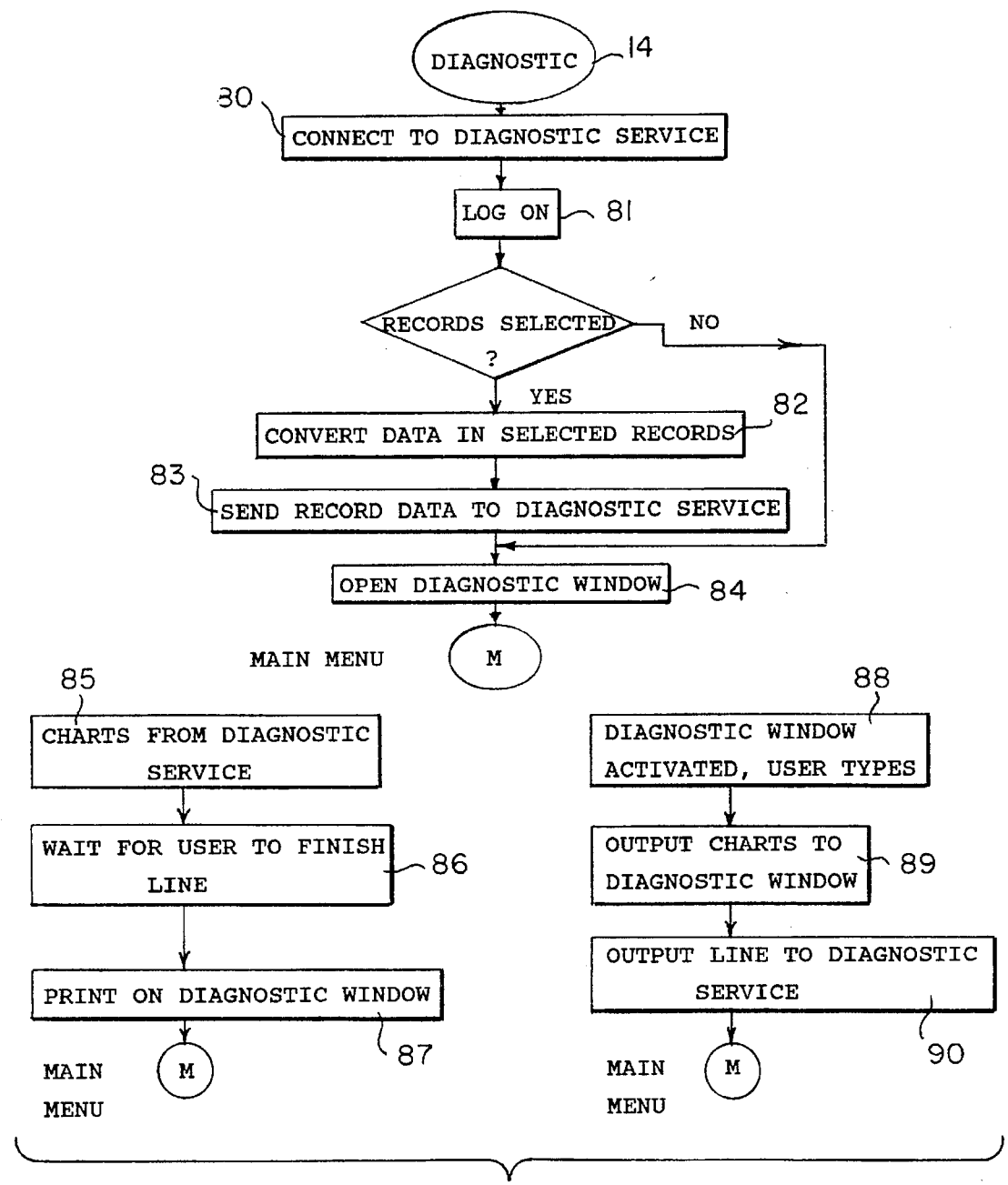
FIG. 8 is a flow chart of the Diagnostic Facility interface.

Another main menu selection is Diagnostic 14 as shown in FIG. 8. This option allows the user to automatically connect 80 to an automatic medical diagnostic service computer. The service network address or phone number is stored as a global preference, as is the sequence of commands required to log onto 81 the service. The command opens up a text window 84 with a scroll bar. Whenever the window is activated 88, any typed characters are sent to the diagnostic service 90 and simultaneously echoed to the bottom of the window's text 89.

Characters emanating from the service 85 are also appended to the window's text, but in a different style (e.g. color). The display of messages from the diagnostic service is deferred 86 until the HCS user types a complete line of text into window 84, so that characters from both sources are not interleaved within a line.

An advanced option allows the user to select (by highlighting) one or more records or record summaries from the History window before activating the Diagnostic operation. The information within these records is then formatted 82 as required by the particular service, and is automatically sent to the service 83.

Another main menu operation, Add File 23, allows the user to add a data file to the record. This file can be textual, sampled sound, image or video data. The data may be a file on the CP 2 or a file already on a RDSF 7 (with a known data identifier code). If the file is already located on a RDSF 7, the data identifier is simply added to the record, along with text identifying what the data represents. If the data exists as a file on the CP 2, then the data may, if the file is sufficiently small, be added directly to a record. Otherwise, it is automatically sent to a user-defined (via global preference) RDSF 7, and the identifier that is returned by the RDSF 7 is entered into the record, together with a text description. The CP 2 may function as the RDSF 7.

Finally, such data files may be created from within the CP 2 program by means of drivers for peripherals such as image scanners, audio input samplers, and video frame grabbers. The data entered from these devices are automatically written to a file on the hard disk system.

Another main menu operation 26b involves listing the pharmaceuticals prescribed to the patient. This allows the HCS to see at a glance which prescriptions were given to a patient. A new "Prescriptions" window is created in which is listed the drugs prescribed, the dates that the drugs were dispensed, the actual drug dispensed (including the manufacturer if different from the prescription), and when the prescription was set to expire.

Also listed is the number of refills remaining on the prescription. A part of the Prescriptions window is a date field that is similar in operation to the date field of the Search window. The Prescriptions operation involves creating and displaying the window, and scanning the "Prescriptions" field(s) of all records within the specified time frame. If a record exists of a drug being dispensed, that record is associated with the closest earlier prescription of an equivalent drug. It may also be possible to explicitly link these two events by requiring the HCS to enter on the SD 1 the date that the medication or therapy was prescribed.

Based on the prescription data, it ordinarily will be possible to calculate the day on which a drug course is completed, i.e., the calculation will normally be accurate except for patients who deviate from the dosage regimen. This information is entered on the line as well.

Finally, as in the case of the History window and a Record window, clicking on the name of a drug or therapy causes the creation of a text window that displays information about that drug.

It is to be noted that "prescriptions" is primarily intended to mean prescribed pharmaceuticals. However, for purposes of using this invention, that term is deemed synonymous with "drug" and the latter includes all biochemically active substances used by the patient in addition to prescribed pharmaceuticals, including alcohol, nicotine and illicit drugs. This is an important medical point, since numerous persons are discovered in poor mental and physical condition, either in accidents or through loss of shelter and so on. In treating such individuals, as in the case of anyone, the HCS should know the biochemical "mix" taken by the patient. Since alcohol and the other substances have very powerful effect on health, an optimum MH CS must include this information.

Another menu option 24 allows collating various types of data for creating reports or detailed printouts.

The Queue menu operation 24 allows managing one or more data files that are appended with text or images of interest within the CP 2 program. A sub menu of the Queue 24 menu allows creating a new queue file by way of a temporary window used for prompting the user for a file name. The name of each new queue that is defined is added to the queue submenu, and selecting one of these allows any highlighted window data to be added to the end of that queue file. The information can be textual or graphical. If nothing within the activated window is highlighted, the entire window contents are added.

If no window is highlighted, then a new window is created that allows operations to be performed on the selected queue file. These operations include: delete file, print file, delete last added record, and save file under another name.

Other main menu options allow printing 25 the contents of the window that is currently key, and saving 26 window contents to a text file. These commands operate on the window that is currently active and are standard in the well-known "windows" systems and thus, it is not necessary to elaborated them.

One novel feature allows connecting to the CDF 6 and obtaining accounting data and also having the capability to search records 15. This is described in more detail below.

Finally, the remaining operations allow a user to close a history 28, and quit 12a the program. If a new record was created, then that record is written to the end of the file that was the source of the history, and that record is also sent to the CDF 6.

CDF SOFTWARE

Figure 9:
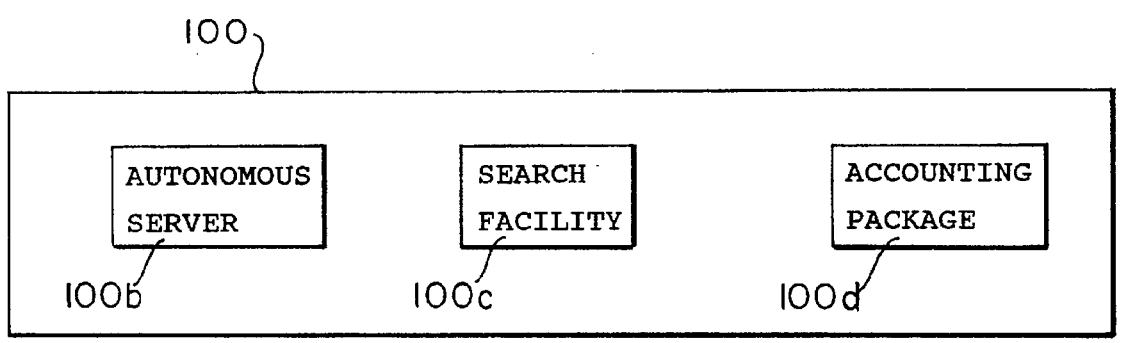
FIG. 9 is a block diagram of the components of the Central Data Facility (CDF).

The Central Data Facility (CDF) software 100 is divided into three distinct components, as shown in FIG. 9: An autonomous server 100b that autonomously accepts and dispenses histories and accounting information over a temporary communication channel; A search mechanism 100c that allows epidemiological studies to be carried out on the medical history database; and an accounting package 100d that can be used to reimburse the HCS for sending each record.

If a given patient is insured by a Health Insurance entity or Health Maintenance Organization, the accounting package can be used so that such insurers directly reimburse the HCS who input the patient's record for developing the patient's record.

Figure 10:
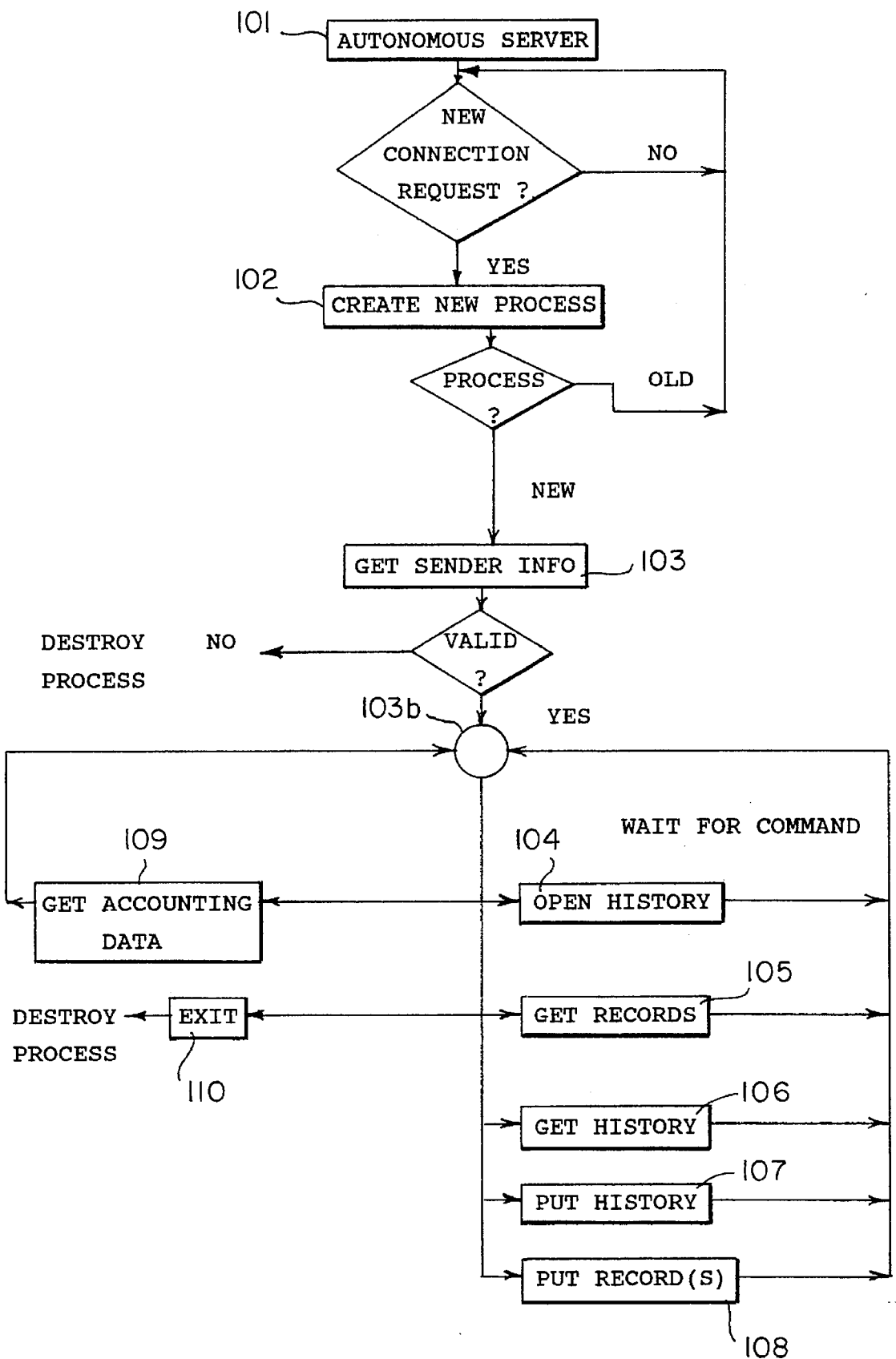
FIG. 10 is a flow chart of the operation of the CDF Autonomous Server.
Figure 11:
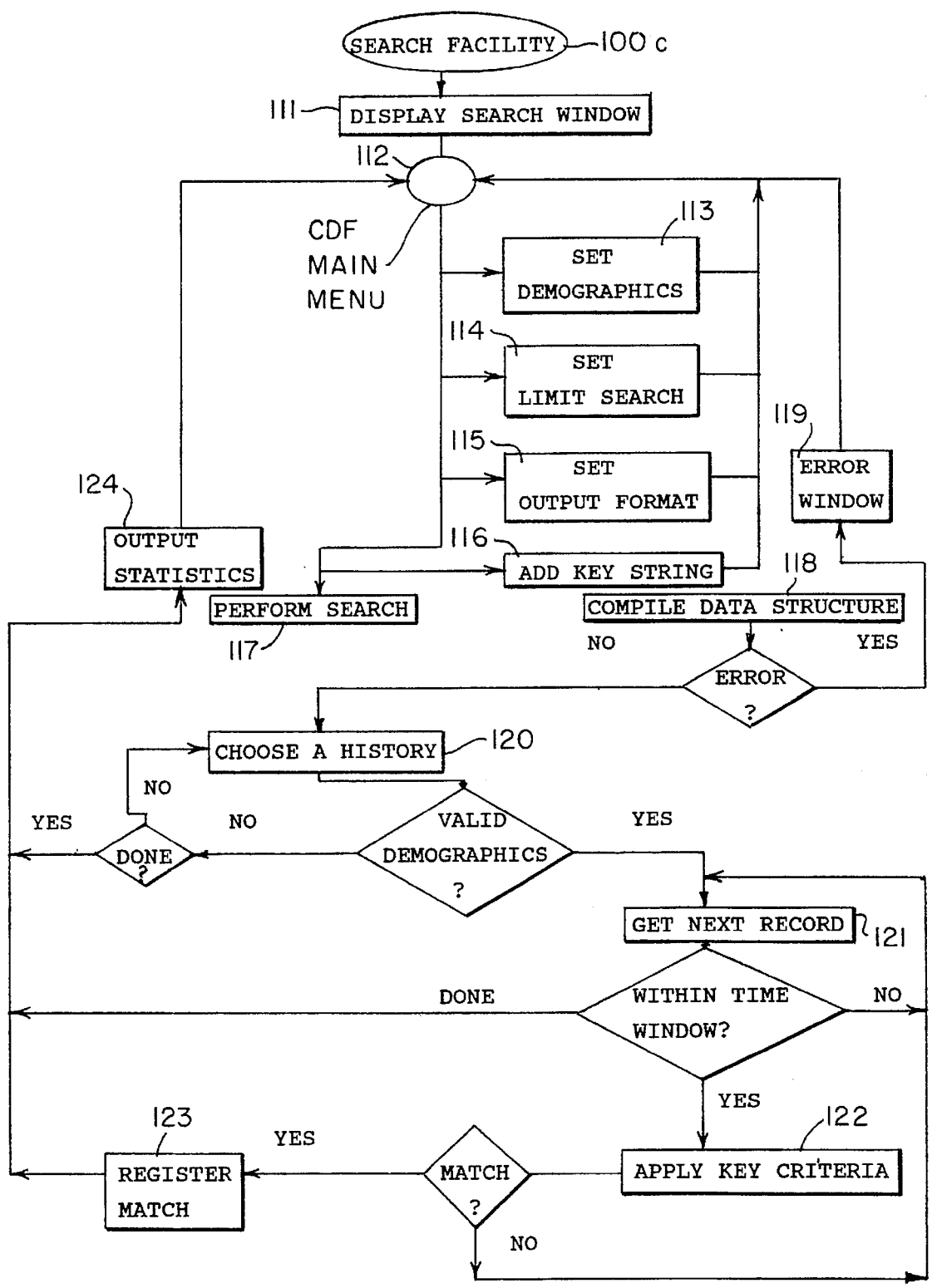
FIG. 11 is a flow chart of the Search Facility component of the CDF.

The CDF autonomous server 100b is multitasking: it can service many CP 2 connections simultaneously (FIG. 10).

Connection requests, which are always initiated by the CP 2, cause the server 100b to create a new operating system process 102 to interact with the caller. A code identifying the HCS originating the connection, and a password (preferably using a standard public key encription mechanism to ensure security) is then received from the caller 103. If this information validates the caller, the process executes a wait loop 103b while awaiting a request. The server carries out only a few simple request types, which can easily be programmed by anyone skilled in the art.

The Open History 104 request simply causes the server to locate a history in its memory, based on the history's ID code, and to keep a file pointer open to the data. If the request indicates that the record is a new one, the system verifies that the ID is not already in use.

The Get Records request 105 specifies that all records between a start date (and time) and an end date (and time) be transferred to the CP 2. The complete text of the records is sequentially dumped to the CP 2.

The Put Records request 108 causes records to be transferred to the CDF 6 and appended to the open MH file.

The Get History File request 106 dumps the specified history file (medical history, critical information file, etc.) to the CP 2. Conversely, the Put History File 107 request reverses this process, with the exception that a medical history file cannot be written unless the record is new.

The Get Accounting Data 109 request allows the caller to interact with the accounting package 100d. Allowed requests include reading the reimbursement record of the caller, and obtaining general purpose comments, memos and statistics from the CDF. 6

The second component of CDF software is the search facility 100c. This takes the basic form of the search command of the CP 2 program, but with several extensions. The program starts by displaying a Search window 111, and a main menu 112. The search window is similar to the Search window 64 of the CP 2 program. One important extension allows collating data over many subjects. Additional features allow limiting the search by specifically reducing the number of records that are examined.

A Demographics main menu operation 113 causes a Demographics window to be opened in which the user can specify the target population of the search, by use of a Demographics window (not shown). Specific characteristics of the patient, such as age, race and gender may be specified in the fields of this window in order to limit the search, or so to study particular populations or age-related effects. Such characteristics are assumed to be in the first record of the history.

After a user initiates the Search 117, the syntax is checked during compilation of the internal logical data software 118. Errors are reported to the user 119.

The Limit Search menu operation 114 allows the user to specify in another window the number of histories to search, an elapsed execution time after which the search will terminate, and the order in which records are searched (e.g. alphabetically, by ID, by position on the disk, or randomly).

The criteria in the Search window 111 is applied to all examined histories 120 that meet the above criteria. All of the features of the search key string described in the CP 2 search operation (FIG. 7) apply here: each record is read 121, and the date is compared with the date range in the Search window 111. If the record is within the date range, the key criteria are applied 122, resulting in a match determination. Each match is then registered 123 for later statistics output.

There are also several extensions to the syntax. First, more than one key string can be specified, and the relationship between key strings can be specified as AND, OR or "independent". (The "independent" relationship results in independent match operations for each key string.) This allows a simplified notation of highly complex search criteria, and allows multiple searches to be carried out for the target population (in the case of the independent relationship). Each additional key string can be invoked by use of the menu command Add Key String 116.

Second, a date range can be included for each key word that is presented within parenthesis immediately preceding the field identifier. Dates can be absolute, relative, or patient age.

Third, a mechanism is added for temporally marking the times that specified events occur within a history, and allowing record searches to be conducted relative in time to these events. This is useful for such studies as detecting possible side-effects of prescriptions or complications of surgery. To achieve this capability, trigger events can be defined, and a search for response effects can be constrained to a time window relative to the trigger event.

A trigger event is defined by associating a trigger identifier with the key clause that identifies the trigger event (e.g. a heart attack). For example, this may take the form:

$2=(30 y,40 y) diagnosis:coronary

Indicating that trigger identifier number 2 should take on the dates of all diagnosed coronary conditions that occurred in a patient between the ages of 30 and 40. Note that the trigger identifier can take on more than one date, if the key clause evaluates to true in the case of more than one record.

The second part of this capability allows specifying a time window relative to the trigger event. This follows the format of the normal time frame syntax, except that the limits are relative to the trigger identifier. Thus, the complete search syntax to find all dizziness complaints within four years of a heart attack would be:

$2=(30 y,40 y) diagnosis:coronary AND ($2,$2+4 y) symptom:dizzy.

After the search has terminated, a statistical record is generated. The main menu operation Output Format 115 can be used to specify the form of the statistics. The IDs, dates and times of all matched records can be conditionally saved in a file. Statistics are output to a file and to the user 124 by way of a Results window 124. These statistics include the number of histories searched, the number of histories meeting the demographic criteria, and the number of histories that were matched.

Conditionally, the program will also output a histogram of the number of records that were matched within all histories that contained at least one record that matched.

The third and final component of CDF software is an automated accounting package 100d that can track reimbursements due to the sender of medical history records, usually, the HCS. These reimbursements may be based on the receipt of records, if the CDF facility manager is interested in collecting history data for epidemiological or case studies. The reimbursements may be based on a weighted combination of the number of records sent, the number of words sent, and the detail of each record. There may be a penalty for record in which certain information is omitted, or payment may be deferred until a particular record is completed by the sender.

The system keeps a running record of the reimbursable amounts for each registered sender, and periodically prints out the totals due each sender. Payment information may be transferred directly to a financial package capable of printing checks automatically, or initiating a wire transfer to the sender's bank account.

The accounting package is also capable of reimbursing the sender for time, tests and procedures, if the CDF operator is a health insurance or health maintenance organization or agent thereof (collectively called "insurer" sometimes herein), and the record concerns a prescriber of the organization. The amount to be reimbursed for each test, procedure, or other service may be requested in the record, in which case the accounting package verifies that the costs do not exceed limits. Otherwise, if the organization sets fixed reimbursement costs for each test, procedure or service, then the reimbursement information may be extracted automatically from the record. Finally, the system is also capable of sending the prescriber a list of the services, so as to cut down on fraud and errors. All such reimbursement costs are added to the reimbursement record of the sender.

The CDF is also capable of invoicing the insurer (assuming the CDF is not owned by the insurer) and, optionally, directing payment(s) by the insurer to parties designated by the CDF. Conversely, the CDF can also forward directions to the insurer to pay designated entities.

I claim:

1. A medical history computer system (CS) usable by a health care specialist (HCS) for recording the medical history (MH) of persons comprising:

A. An electronic computer (CP) having:
   a. a memory (M) including a random access memory (RAM) and means for permanent memory (PM);
   b. means for storing MH data (MHD) for each person in the M;
   c. means for receiving a MH storage device (SD), said SD being no larger than a normal human hand and preferably the size of a credit card, and which is optimally routinely carried daily by each person whose MH is recorded;
   d. means for transferring MHD for each person from/to the M to the SD;
   e. means for adding new MH data (NMHD) for each such person to the SD by inputting the new MH data in the RAM;
   f. means for transferring the NMHD for each person onto the SD for each such person, whereby said NMHD becomes part of the MHD stored on the SD for that person;

B. said CS also having a monitor for the visual display of the MHD on the RAM;

C. Said CS including an MH program for storing a person's MH, said program comprising means for creating a MH file for the person, for modifying that MH file, and for creating a critical information file (CIF) for that person;

D. said CS further including means for searching for specific information in a MH based on a character string supplied by the HCS or other source, wherein the CS includes a program comprising:
   a. means for searching the MH for specific words that are specified in the character string;
   b. means for interpreting logic operators such as AND and OR in the character string in order to determine whether a particular character string that contains multiple words connected by said logic operations can be successfully matched with a MH that contain some of the said specified words, and
   c. means for searching for each word given in the character string in terms of such word per se and also its synonyms and other related words.

2. The invention of claim 1 further including means for searching a MH for selected data and plotting that data in a graph.

* * * * *